(12) United States Patent
Woods (10) Patent No.: US 11,966,661 B2
(45) Date of Patent: Apr. 23, 2024

(54) AUDIO CONTENT SERVING AND CREATION BASED ON MODULATION CHARACTERISTICS

(71) Applicant: BrainFM, Inc., Brooklyn, NY (US)

(72) Inventor: Kevin J. P. Woods, Brooklyn, NY (US)

(73) Assignee: BrainFM, Inc., Brooklyn, NY (US)

( * ) Notice: Subject to any disclaimer, the term of this patent is extended or adjusted under 35 U.S.C. 154(b) by 0 days.

(21) Appl. No.: 17/505,453

(22) Filed: Oct. 19, 2021

(65) Prior Publication Data

US 2023/0122796 A1 Apr. 20, 2023

(51) Int. Cl.
| | |
|---|---|
| G06F 3/16 | (2006.01) |
| A61M 21/00 | (2006.01) |
| G09B 5/06 | (2006.01) |
| G10K 15/02 | (2006.01) |

(52) U.S. Cl.
CPC .............. *G06F 3/165* (2013.01); *G10K 15/02* (2013.01); *A61M 21/00* (2013.01); *A61M 2021/0027* (2013.01); *G09B 5/06* (2013.01)

(58) Field of Classification Search
CPC ........ G06F 3/165; G10K 15/02; A61M 21/00; A61M 2021/0027; G09B 5/06
See application file for complete search history.

(56) References Cited

U.S. PATENT DOCUMENTS

| | | | |
|---|---|---|---|
| 3,712,292 A | 1/1973 | Zentmeyer | |
| 4,141,344 A | 2/1979 | Barbara | |
| 4,191,175 A | 3/1980 | Nagle | |
| 4,227,516 A | 10/1980 | Meland et al. | |
| 4,315,502 A | 2/1982 | Gorges | |
| 4,777,529 A | 10/1988 | Schultz et al. | |
| 5,135,468 A | 8/1992 | Meissner | |
| 5,213,562 A | 5/1993 | Monroe | |
| 5,289,438 A | 2/1994 | Gall | |
| 5,586,967 A | 12/1996 | Davis | |

(Continued)

OTHER PUBLICATIONS

U.S. Appl. No. 11/251,051, US 2007-0084473 A1, Apr. 19, 2007, Issued.

(Continued)

*Primary Examiner* — Carolyn R Edwards
*Assistant Examiner* — Kuassi A Ganmavo
(74) *Attorney, Agent, or Firm* — Akerman LLP (57) ABSTRACT

Techniques (methods and devices) for audio content serving and creation based on modulation characteristics are disclosed. The techniques include receiving user-associated data related to a user; determining one or more desired modulation characteristic values based on the user-associated data; obtaining a set of one or more target audio tracks, wherein each target audio track represents at least one or more modulation characteristic values; comparing the desired modulation characteristic values with the modulation characteristic values of at least one target audio track from the set of one or more target audio tracks; selecting a target audio track from the at least one target audio track based on the comparing, wherein the modulation characteristic values of the target audio track substantially match the desired modulation characteristic values; and playing the target audio track.

21 Claims, 7 Drawing Sheets

(56) References Cited

U.S. PATENT DOCUMENTS

| | | | |
|---|---|---|---|
| 7,674,224 B2 | 3/2010 | Hewett | |
| 2001/0049480 A1 | 12/2001 | John et al. | |
| 2002/0005108 A1* | 1/2002 | Ludwig | G10H 1/0058 |
| | | | 84/600 |
| 2003/0089218 A1* | 5/2003 | Gang | G11B 27/34 |
| | | | 84/615 |
| 2007/0084473 A1 | 4/2007 | Hewett | |
| 2007/0291958 A1 | 12/2007 | Jehan | |
| 2008/0097633 A1* | 4/2008 | Jochelson | A63B 71/0686 |
| | | | 700/94 |
| 2010/0005686 A1 | 1/2010 | Russell | |
| 2010/0056854 A1 | 3/2010 | Chang | |
| 2010/0188580 A1 | 7/2010 | Paschalakis et al. | |
| 2011/0169603 A1* | 7/2011 | Fithian | G06Q 10/00 |
| | | | 340/5.52 |
| 2012/0251989 A1 | 10/2012 | Wemore | |
| 2013/0046546 A1 | 2/2013 | Uhle et al. | |
| 2013/0216055 A1 | 8/2013 | Wanca | |
| 2014/0223462 A1 | 8/2014 | Ainnone et al. | |
| 2014/0330848 A1* | 11/2014 | Chen | G06F 16/24578 |
| | | | 707/749 |
| 2015/0016613 A1 | 1/2015 | Atwater et al. | |
| 2015/0199010 A1 | 7/2015 | Coleman et al. | |
| 2015/0297109 A1 | 10/2015 | Garten et al. | |
| 2015/0351655 A1 | 12/2015 | Coleman | |
| 2015/0356876 A1* | 12/2015 | Wang | G09B 5/06 |
| | | | 434/236 |
| 2016/0143554 A1 | 5/2016 | Lim et al. | |
| 2016/0372095 A1 | 12/2016 | Lyske | |
| 2017/0024615 A1 | 1/2017 | Allen et al. | |
| 2017/0043236 A1* | 2/2017 | Li | B62J 45/416 |
| 2017/0124074 A1* | 5/2017 | Cama | G06F 16/686 |
| 2017/0339484 A1 | 11/2017 | Kim | |
| 2017/0371961 A1 | 12/2017 | Douglas | |
| 2018/0315452 A1 | 11/2018 | Shi et al. | |
| 2020/0074982 A1 | 3/2020 | McCallum | |
| 2020/0213790 A1* | 7/2020 | Osborne | G06F 16/683 |

OTHER PUBLICATIONS

U.S. Appl. No. 15/857,065, US 2019/0201658 A1, Jul. 4, 2019, Issued.

U.S. Appl. No. 16/276,961, US 2020-0265827 A1, Aug. 20, 2020, Pending.

U.S. Appl. No. 17/366,896, filed Jul. 2, 2021, Pending.

Greenburg et al. "The Modulation Spectrogram: In Pursuit of an Invariant Representation of Speech", Presented at ICASSP-97, vol. 3, pp. 1647-1650.

Moritz, et al. "An Auditory Inspired Amplitude Modulation Filter Bank for Robust Feature Extraction in Automatic Speech Recognition", IEEE/ACM Transactions on Audio, Speech, and Language Processing, vol. 23, No. 11, Nov. 2015.

Singh et al. Modulation Spectra of Natural Sounds and Ethological Theories of Auditory Processing, J. Acoust. Soc. Am, 114 (6), Pt. 1, pp. 3394-3411, Dec. 2003.

International Search Report issued in International Applicatio No. PCT/US2020/017788 dated Apr. 29, 2020, 2 pages.

Written Opinion issued in International Applicatio No. PCT/US2020/017788 dated Apr. 29, 2020, 5 pages.

* cited by examiner

AUDIO CONTENT SERVING AND CREATION BASED ON MODULATION CHARACTERISTICS

RELATED APPLICATIONS

This application is related to U.S. Pat. Nos. 7,674,224, 10,653,857, U.S. Patent Publication No. 2020/0265827, and U.S. patent application Ser. No. 17/366,896, all of which are incorporated herein by reference.

BACKGROUND

For decades, neuroscientists have observed wave-like activity in the brain called neural oscillations. Various aspects of these oscillations have been related to mental states including attention, relaxation, and sleep. The ability to effectively induce and modify such mental states by noninvasive brain stimulation is desirable.

OVERVIEW

Modulation in sound drives neural activity and can support mental states. Sounds that have similar modulation-domain representations may have similar effects on the brain. Analysis of modulation characteristics of pre-existing tracks can allow tracks to be selected to achieve desired mental states, with or without further modification of those tracks. In example embodiments, the present disclosure describes a personalization of audio content based on user-related characteristics and/or the determined effectiveness to a user of similar audio content to achieve a desired mental state.

In example embodiments, the present disclosure provides techniques for serving and creating audio for playback to induce a mental state based on what is effective/ineffective for a user. A measure of effectiveness is not limited to a binary measurement (i.e., effective or ineffective) but can be based on a scale of measurement (e.g. analog rating—X/5 stars, X level of effectiveness as judged by sensors, listening time, etc.).

In example embodiments, the effectiveness of audio in helping the user reach a desired mental state can be determined by user input. Additionally, or alternately, the effectiveness can be determined without an active input by the user. For example, whether an audio was effective to help the user sleep better (desired mental state) can be determined either directly (by asking the user) or indirectly using a smart device such as, for example, an Oura ring (e.g., sleep score, sleep parameters, etc.), an Apple watch (e.g., sleep parameters), a smartphone (e.g., was phone used during 'sleep time'), etc. In another example, a clinical or academic sleep study performed with participants who are not the user, may be used to determine the effectiveness of an audio to help the user sleep better. Other examples exist.

Another non-limiting example, whether an audio was effective to help the user stay focused can be determined either directly (by asking the user) or indirectly using a smart device such as a smart watch (e.g., did the user stay seated?), smart phone (e.g., did the user use their phone during focus time?), etc. In yet another non-limiting example, whether an audio was effective to help the user relax can be determined either directly (e.g., by asking the user) or indirectly using a smart device such as an Oura ring (e.g., was their resting heart rate lower than a threshold?), smart watch (e.g., did their heart rate and blood pressure decrease during a relaxing track?), etc.

In example embodiments, user preference regarding a type of audio can also be taken into consideration. The combination of preferred audio & effective modulation characteristics tailored to a desired mental state may provide a better desired response than an arbitrary audio with modulation characteristics. For example, a user's preferred music genre (e.g., Country, Jazz, Reggae, Pop, etc.) may be taken into consideration. Alternatively, or additionally, a user's artist preference (e.g., Willie Nelson, John Coltrane, Bob Marley, Kanye West, etc.) may be taken into consideration. Alternatively, or additionally, a user's preferred audio characteristic(s) (e.g., brightness, upbeat, dissonance, etc.) may also be used.

In example embodiments, amplitude modulation analysis can be performed by considering the frequency content of sound envelopes (i.e., the 'outline' of broadband or sub band waveforms). Amplitude modulation in sound can drive rhythmic activity in the brain, which may be leveraged to support mental states like focus, sleep, relaxation, meditation, physical exertion (e.g., exercise), and the like. Amplitude modulation analysis is distinct from frequency domain analysis in that the former describes slow rates of change (under 1 kHz) and involves the modulation of a carrier signal whereas the latter describes the sinusoidal components making up the signal itself. Other recommendation systems may not have awareness of modulation-domain analysis (which in the human auditory system involves a modulation-frequency filter bank in the brainstem, similar to the audio-frequency filter bank in the cochlea) and its effects on mental states, and so such recommendation systems may not use modulation-domain analysis and may not target mental states with amplitude modulation.

In example embodiments, modulation-frequency domain analysis (i.e., extraction of modulation characteristics) identifies properties of amplitude fluctuations at rates between 0 Hz-1000 Hz at any audio frequency, whereas audio-frequency analysis quantifies energy at frequencies across the range of human hearing, from 20 Hz-20 kHz.

In example embodiments, the following techniques can be used for extracting the modulation characteristics from audio: 1) Fast Fourier Transform (fft) of broadband or subband envelopes; 2) modulation domain bandpass filtering; and 3) visual filtering on spectrographic representation. Each of these techniques are described in detail subsequently.

Some example embodiments include: receiving, by a processing device, user-associated data related to a user; determining, by the processing device, one or more desired modulation characteristic values based on the user-associated data; obtaining, by the processing device, a set of one or more target audio tracks, wherein each target audio track represents at least one or more modulation characteristic values; comparing, by the processing device, the desired modulation characteristic values with the modulation characteristic values of at least one target audio track from the set of one or more target audio tracks; selecting, by the processing device, a target audio track from the at least one target audio track based on the comparing, wherein the modulation characteristic values of the target audio track substantially matches the desired modulation characteristic values; and playing, by the processing device, the target audio track.

In various example embodiments, the user-associated data can comprise self-reported user data and/or a target mental state of the user. The self-reported user data can include user information regarding sound sensitivity, age, ADHD and/or preferences for a target audio track and/or preferred audio characteristics. The target mental state can comprise focus, relax, sleep, exercise, and/or meditation. The user-associated data can comprise an audio content with an effectiveness measurement such that the effectiveness measurement indicates an effectiveness of the audio content for the user.

Some example embodiments can include determining, by the processing device, one or more modulation characteristic values of the audio content based on modulation synthesis parameters and/or modulation domain analysis. Other example embodiments can include modifying, by the processing device, the one or more modulation characteristic values of the audio content to match the desired modulation characteristic values based on the effectiveness measurement of the audio content. The modifying can include dynamically modifying modulation characteristics of the audio content.

Some example embodiments can further include selecting, by the processing device, a subsequent target audio track from the set of one or more target audio tracks based on the comparing such that the modulation characteristic values of a beginning portion of the subsequent target audio track aligns in a predetermined manner with an end portion of the target audio track; and chaining, by the processing device, the target audio track and the subsequent target audio track.

Some example embodiments include: receiving, by a processing device, a user's target mental state; receiving, by the processing device, a reference audio content with an effectiveness measurement that indicates an effectiveness of the reference audio content to achieve the target mental state for the user; determining one or more modulation characteristic values of the reference audio content and/or one or more additional audio parameter values of the reference audio content; obtaining, by the processing device, a set of one or more target audio tracks, wherein each target audio track includes one or more modulation characteristic values and one or more additional audio parameter values; comparing, by the processing device, for at least one target audio track from the set of one or more target audio tracks, the modulation characteristic values of the reference audio content with the modulation characteristic values of the at least one target audio track and the additional audio parameter values of the reference audio content with the additional audio parameter values of the at least one target audio track; and modifying, by the processing device, the at least one target audio track from the set of one or more target audio tracks based on the comparing such that the modulation characteristic values of the at least one target audio track substantially match the modulation characteristic values of the reference audio content and the audio parameter values of the at least one target audio track substantially match the additional audio parameter values of the reference audio content.

In some embodiments, a processing device comprising a processor and associated memory is disclosed. The processing device can be configured to: receive user-associated data related to a user; determine one or more desired modulation characteristic values based on the user-associated data; obtain a set of one or more target audio tracks, wherein each target audio track represents at least one or more modulation characteristic values; compare the desired modulation characteristic values with the modulation characteristic values of at least one target audio track from the set of one or more target audio tracks; select a target audio track from the at least one target audio track based on the comparing, wherein the modulation characteristic values of the target audio track substantially match the desired modulation characteristic values; and play the target audio track.

In some embodiments, a processing device can be configured to: receive a user's target mental state; receive an audio content with an effectiveness measurement that indicates an effectiveness of the audio content to achieve the target mental state for the user; determine one or more modulation characteristic values of the audio content and one or more additional audio parameter values of the audio content; obtain a set of one or more target audio tracks, wherein each target audio track includes one or more modulation characteristic values and one or more additional audio parameter values; compare, for at least one target audio track from the set of one or more target audio tracks, the modulation characteristic values of the reference audio content with the modulation characteristic values of the at least one target audio track and the additional audio parameter values of the reference audio content with the additional audio parameter values of the at least one target audio track; and modify the at least one target audio track from the set of one or more target audio tracks based on the comparing such that the modulation characteristic values of the at least one audio track substantially match the modulation characteristic values of the reference audio content and the audio parameter values of the at least one target audio track match the additional audio parameter values of the reference audio content.

BRIEF DESCRIPTION OF DRAWINGS

Other objects and advantages of the present disclosure will become apparent to those skilled in the art upon reading the following detailed description of exemplary embodiments and appended claims, in conjunction with the accompanying drawings, in which like reference numerals have been used to designate like elements, and in which:

The figures are for purposes of illustrating example embodiments, but it is understood that the inventions are not limited to the arrangements and instrumentality shown in the drawings. In the figures, identical reference numbers identify at least generally similar elements.

DESCRIPTION

The present disclosure describes systems, methods, apparatuses and computer executable media for personalizing, for a user, a selection of one or more target audio tracks for playback. The personalizing can be based on one or more of the following aspects: a user-associated data (e.g., target mental state of a user, self-report data, behavioral data for a user, effectiveness ratings of audio tracks previously played by a user, sensor-input values for a sensor associated with a user, etc.), a reference audio track, and modulation characteristics of the one or more target audio tracks, whereby the modulation characteristics can be based on modulation synthesis parameters and/or modulation domain analysis of the one or more target audio tracks. The target audio tracks can be selected for a user based on their effectiveness towards a user's desired mental state based on their modulation characteristics, rather than mere aesthetic rating and/or music parameters (e.g., tonality, instrumentation, chords, timbre, etc.) as provided by known services.

In example embodiments, modulation characteristics may include depth of modulation at a certain rate, the rate itself, modulation depth across all rates (i.e., the modulation spectrum), phase at a rate, among others. These modulation characteristics may be from the broadband signal or in subbands (e.g., frequency regions, such as bass vs. treble). The subbands used may be based on cochlear subbands (i.e., the frequency decomposition employed at the human auditory periphery). Audio/audio track/audio content, as used herein, can refer to a single audio element (e.g., a single digital file), an audio feed (either analog or digital) from a received signal, or a live recording. As used herein, audio/audio track/audio content can be a temporal portion of an audio track/content (e.g., one or more snippets of an audio track/content), a spectral portion of an audio track/content (e.g., one or more frequency bands or instruments extracted from an audio track/content) or a complete audio track/content.

In the past, technologies have been targeted to the full range of audio frequencies perceptible to humans. The present disclosure describes technologies that may target specific subregions of that range. In various exemplary embodiments described herein, the modulation can be effective when applied at predetermined frequencies, which are associated with known portions of the cochlea of the human ear and may be referenced in terms of the cochlea, or in terms of absolute frequency. For example, predetermined frequencies can be associated with portions of the cochlea of the human ear that are more sensitive for neuromodulation. Additionally, predetermined frequencies can be associated with portions of the cochlea of the human ear that are perceived less sensitively such that the modulation is not distracting to a user. Note that these are specific regions within the full range of human hearing. Furthermore, the presently disclosed techniques may provide for a selection of modulation characteristics configured to target different patterns of brain activity. These aspects are subsequently described in detail.

In various exemplary embodiments described herein, audio can be modulated in order to affect patterns of neural activity in the brain to affect perception, cognition, action, and/or emotion. Modulation can be added to audio (e.g., mixed) which can in turn be stored and retrieved for playback at a later time. Modulation can be added to audio (e.g., mixed) for immediate (e.g., real-time) playback. Modulated audio playback may be facilitated from a playback device (e.g., smart speaker, headphone, portable device, computer, etc.) and may be single or multi-channel audio. Modulated audio playback may be facilitated through a playback device that transforms the audio into another sensory modality such as vibration or modulated light, rather than being an audible signal. Users may facilitate the playback of the modulated audio through, for example, an interface on a processing device (e.g., smartphone, computer, etc.). These aspects are subsequently described in detail.

Figure 1:
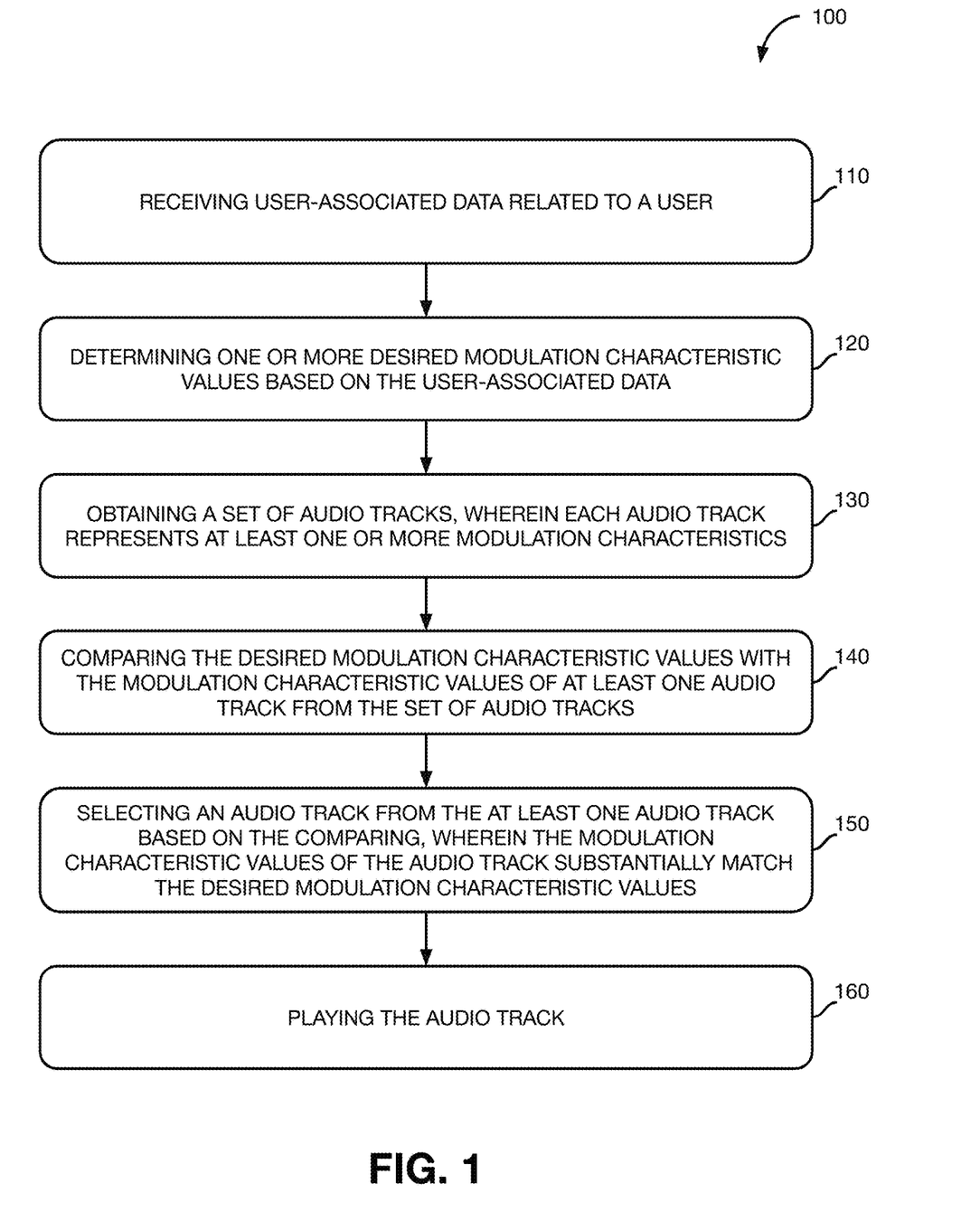
FIG. 1 is a flowchart of a method according to an example embodiment of the present disclosure.

FIG. 1 illustrates an example method 100 performed by a processing device (e.g., smartphone, computer, smart speaker, etc.) according to an example embodiment of the present disclosure. The method 100 may include one or more operations, functions, or actions as illustrated in one or more of blocks 110-160. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

Method 100 can include a block 110 of receiving user-associated data. In example embodiments, user-associated data can comprise self-report data such as, for example, a direct report or a survey, e.g., ADHD self-report (e.g., ASRS survey or similar), autism self-report (e.g., AQ or ASSQ surveys or similar), sensitivity to sound (e.g., direct questions), genre preference (e.g., proxy for sensitivity tolerance), work habits re. music/noise (e.g., proxy for sensitivity tolerance), and/or history with a neuromodulation. Self-report data can also include time-varying reports such as selecting one's level of relaxation once per minute, leading to dynamic modulation characteristics over time in response. User-associated data can also comprise other user surveys such as, for example, onboarding questions (e.g., questions of users new to the presently disclosed system/methods etc.), personality questionnaires (e.g. questions related to personality of a user), etc.

In example embodiments, user-associated data can comprise effectiveness ratings of audio tracks previously played by a user. The effectiveness ratings can be based on explicit ratings provided by the user (e.g., the user provides a 5-star rating to a track, etc.) or implicit ratings (e.g., a user skipping the track repeatedly reflects a lower rating, a user repeatedly playing a track or submitting a track to the server reflects a higher rating, etc.).

In example embodiments, user-associated data can comprise behavioral data/attributes such as user interests, a user's mental state, emotional state, etc. User-associated data can include data about the user's current temporary condition (i.e., states) and/or the user's unchanging persistent conditions (i.e., traits). User-associated data can be obtained from various sources such as user input, the user's social media profile, etc. User-associated data can comprise factors external to, but related to, the user such as, for example, the weather at the user's location; the time after sunrise or before sunset at the user's location; the user's location; or whether the user is in a building, outdoors, or a stadium.

In example embodiments, user-associated data can comprise sensor-input values obtained from one or more sensors associated with the user. The sensors may include, for example, an inertial sensor such as an accelerometer (e.g., phone on table registers typing which may be used as a proxy for productivity); a galvanic skin response (e.g., skin conductance); a video or image camera (e.g., user-facing: eye tracking, state sensing; outward-facing: environment identification, movement tracking); and a microphone (e.g., user-sensing: track typing as proxy for productivity, other self-produced movement; outward-sensing: environmental noise, masking, etc.). The sensors may include a physiological sensor such as, for example, a heart rate monitor; a blood pressure monitor; a body temperature monitor; an EEG; a MEG (or alternative magnetic-field-based sensing); a near infrared sensor (fnirs); and/or bodily fluid monitors (e.g., blood or saliva for glucose, cortisol, etc.).

The sensors may include real-time computation. Non-limiting examples of a real-time sensor computation include: the accelerometer in a phone placed near a keyboard on a table registering typing movements as a proxy for productivity; an accelerometer detecting movements and reporting a user has started a run (e.g. by using the CMMotionActivity object of Apple's iOS Core ML framework), and microphone detecting background noise in a particular frequency band (e.g., HVAC noise concentrated in bass frequencies) and reporting higher levels of distracting background noise. In an example embodiment, where the audio content includes background noise, determining modulation characteristics (described subsequently) can be optional.

The sensors can be on the processing device and/or on an external device and data from the sensor can be transferred from the external device to the processing device. In one example, the sensor on a processing device, such as, for example, an accelerometer on a mobile phone, can be used to determine how often the phone is moved and can be a proxy for productivity. In another example, the sensor on an activity tracker (e.g., external device) such as, for example, an Oura ring or Apple watch, can be used to detect if the user is awake or not, how much they are moving, etc.

In some embodiments, the sensors can be occasional-use sensors used to calibrate the music to stable traits of the user or their environment. For example, a user's brain response to modulation depth can be measured via EEG during an onboarding procedure which may be done per use or at intervals such as once per week or month. In other embodiments, the sensors can be responsive to the user's environment. For example, characterizing the acoustic qualities of the playback transducer (e.g., for headphones/speakers) or the room using a microphone, electrical measurement, an audiogram, or readout of a device ID. The sensors can measure environmental factors that may be perceived by the user such as, for example, color, light level, sound, smell, taste, and/or tactile.

In some embodiments, behavioral/performance testing can be used to calibrate the sensors and/or to compute sensor-input values. For example, a short experiment for each individual to determine which modulation depth is best via their performance on a task. Similarly, external information can be used to calibrate the sensors and/or to compute sensor-input values. For example, weather, time of day, elevation of the sun at user location, the user's daily cycle/circadian rhythm, and/or location. Calibration tests, such as calibrating depth of modulation in the music to individual users' sound sensitivity based on a test with tones fluctuating in loudness can also be used to calibrate the sensors and/or to compute sensor-input values. Each of these techniques can be used in combination or separately. A person of ordinary skill in the art would appreciate that these techniques are merely non-limiting examples, and other similar techniques can also be used for calibration of the music based on sensors.

In some embodiments, the sensor-input value can be sampled at predetermined time intervals, or upon events, such as the beginning of each track or the beginning of a user session or dynamically on short timescales/real-time (e.g., monitoring physical activity, interaction with phone/computer, interaction with app, etc.).

In example embodiments, user associated data can include one or more of a target mental state for the user (e.g., sleep, focus, meditation, etc.), user-associated inputs (e.g., history of subjective reports, effectiveness ratings of previous tracks, onboarding questions, personality questionnaires, behavioral input, sensor input values, etc.), and modulation characteristics of one or more reference audio tracks.

At block 120, one or more desired modulation characteristics values can be determined based on the user-associated data. In example embodiments, modulation rate, phase, depth, and waveform can be four non-exclusive modulation characteristics. Modulation rate can be the speed of the cyclic change in energy, and can be defined, for example, in hertz. Modulation phase is the particular point in the full cycle of modulation, and can be measured, for example, as an angle in degrees or radians. Modulation depth can indicate the degree of amplitude fluctuation in the audio signal. In amplitude modulation, depth can be expressed as a linear percent reduction in signal power or waveform envelope from peak-to-trough, or as the amount of energy at a given modulation rate. Modulation waveform may express the shape of the modulation cycle, such as a sine wave, a triangle wave, or some other custom wave. These modulation characteristics can be extracted from the broadband signal or from subbands after filtering in the audio-frequency domain (e.g., bass vs. treble), by taking measures of the signal power over time, or by calculating a waveform envelope (e.g., the Hilbert envelope).

In example embodiments, modulation characteristic values in the audio can be determined using various techniques. Non limiting examples of such techniques can include Fast Fourier Transform (FFT) on the envelope (e.g., 'waveform outline') techniques, modulation domain bandpass filtering that provides phase and amplitude of modulation, visual filtering on spectrographic representation (e.g., use a spectrogram/cochleagram to run a 2D fourier transform, visual filter like convolution with a gabor patch, etc.), or other known techniques. The FFT and the bandpass filtering techniques can be based on subband envelopes. The visual filtering technique can get subbands via a spectrographic representation.

An example visual filtering of a spectrogram technique is described in: Singh N C, Theunissen F E. Modulation spectra of natural sounds and ethological theories of auditory processing. J Acoust Soc Am. 2003 December; 114(6 Pt 1):3394-411. doi: 10.1121/1.1624067. PMID: 14714819. An example technique for FFT of subband envelopes is described in: Greenberg, S., & Kingsbury, B. E. (1997, April). The modulation spectrogram: In pursuit of an invariant representation of speech. In 1997 IEEE International Conference on Acoustics, Speech, and Signal Processing (Vol. 3, pp. 1647-1650). IEEE. An example technique for modulation filterbank method described in: Moritz, N., Anemüller, J., & Kollmeier, B. (2015). An auditory inspired amplitude modulation filter bank for robust feature extraction in automatic speech recognition. IEEE/ACM Transactions on Audio, Speech, and Language Processing, 23(11), 1926-1937. All of these publications are incorporated in their entirety by reference.

In example embodiments, to determine the desired modulation characteristics, a user may be asked after playing an audio track, "Did this track help you to focus?" and presented with a (e.g., thumbs-up and thumbs-down) selection to choose a response. The user can then be presented target audio content (as subsequently described with respect to blocks 140-160) that has similar modulation characteristics (i.e., to drive brain rhythms similarly) to tracks they rated (e.g., thumbs-up). Similarly, a user may be asked for access to their personal focus-music playlist (e.g., to be used as reference tracks), which can be analyzed to determine what modulation characteristics the user finds effective.

In example embodiments, to determine the desired modulation characteristics, a smart device may communicate with the processing device to provide an evaluation of the effectiveness of a reference track. In one example, one or more messages are transmitted between a first application running on the processing device to a second application (e.g., Oura, Apple Health, FitBit, etc.) on an external device (e.g., smart device such as a smart ring, watch, phone, etc.). The one or more messages may include, among other possibilities, a specific type of mental state and/or activity (e.g., sleep, focus, run, etc.) and a time interval (e.g., start/end time, absolute time, etc.) to make the evaluation. The external device may in turn send one or more messages to the processing device indicating a determined mental state and/or evaluation (e.g., based on information gathered during the time interval). In some embodiments, the first and second applications may be the same. In some embodiments, the external device can be the same as the processing device.

In example embodiments, a user model can be generated based on user-associated data that can include user-related input and the user's target mental state. For example, user-related input can be in the form of one or more of (1) information about the user (ADHD, age, listening preferences, etc.); (2) sensor data; and (3) reference tracks with explicit (e.g., stars) or implicit (e.g., provided to the system) rating. A user's mental state can be explicitly provided, inferred, or assumed by the system.

The user model can be defined over a set of modulation characteristics for a user's desired mental state. The user model can prescribe regions in the modulation-characteristic space that are most effective for a desired mental state. The user model may be a function defining predicted efficacy of music, in a high-dimensional space, with dimensions of modulation rate, modulation depth, audio brightness and audio complexity. The user model may be based on prior research that relates modulation characteristics to mental states. For example, if the user says they have ADHD and are of a particular age and gender, then the user model may incorporate this information to determine desired modulation characteristics for a particular target mental state of the user. The determination may, for example, be based on a stored table or function which is based on prior research about ADHD (e.g., users with ADHD require a relatively high modulation depth). Another non-limiting example for defining and/or modifying a user model can be based on reference tracks and ratings provided by a user. The reference tracks can be analyzed to determine their modulation characteristics. The determined modulation characteristics along with the ratings of those tracks can be used to define or modify the user model.

In example embodiments, the user model can be updated over time to reflect learning about the user. The user model can also incorporate an analysis of various audio tracks that have been rated (e.g., {for effectiveness {focus, energy, persistence, accuracy}, or satisfaction}, positively or negatively). The inputs to generate a user model can include ratings (e.g., scalar (X stars), binary (thumbs up/down)), audio characteristics (e.g., modulation characteristics, brightness, etc.) For example, a user known to have ADHD may initially have a user model indicating that the target audio should have higher modulation depth than that of an average target track. If a user subsequently provides a reference track with a positive indication, and it is determined that the reference track has a low modulation depth (e.g., 0.2 out of 1), then the target modulation depth may be updated in the user model (e.g., to an estimate that a low depth is optimal). If the user subsequently provides three more reference tracks with positive indications, and it is determined that the tracks have modulation depths of 0.8, 0.7, and 0.9, then the target modulation depth may be further updated in the user model (e.g., reverting to an estimate that a high depth is optimal). In this example, the user model represents estimated effectiveness as a function of modulation depths from 0-1.

In example embodiments, the user model can predict ratings over the modulation characteristic space. For example, if each input track is a point in high-dimensional space (e.g., feature values) each of which has been assigned a color from blue to red (e.g., corresponding to rating values); then the prediction of ratings may be determined by interpolating across known values (e.g., target input tracks) to estimate a heatmap representation of the entire space. In another example, regions of the space can be predicted to contain the highest rating values via linear regression (i.e., if the relationships are simple) or machine learning techniques (e.g., using classifiers, etc.).

In example embodiments, the user model can be distinctive both in terms of the features used (e.g., modulation features relevant to effects on the brain and performance, rather than just musical features relevant to aesthetics) and in terms of the ratings, which can be based on effectiveness to achieve a desired mental state such as, for example, productivity, focus, relaxation, etc. rather than just enjoyment.

In example embodiments, the user model can be treated like a single reference input track if the output to the comparison is a single point in the feature space (e.g., as a "target") to summarize the user model. This can be done by predicting the point in the feature space that should give the highest ratings and ignoring the rest of the feature space. In this case the process surrounding the user model may not change.

In certain embodiments, a user model may not be required. For example, if multiple reference tracks and ratings are provided as input, the processing device can forgo summarizing them as a model and instead work directly off this provided data. For example, each library track can be scored (e.g., predicted rating) based on its distance from the rated tracks (e.g., weighted by rating; being close to a poorly rated track is bad, etc). This can have a similar outcome as building a user model but does not explicitly require a user model.

In embodiments where only one reference track is used as input, it may be desirable to forgo a user model altogether, and directly compare the reference track to one or more target tracks. This is similar to a user model based only on the one reference track. If the reference track and the one or more target tracks are compared directly, they can be represented in the same dimensional space. Thus, the audio analysis applied to the reference track should result in an output representation that has the same dimensions as the audio analysis that is applied to the one or more target tracks.

At block 130, a set of one or more target audio tracks or a library of target audio tracks can be obtained. The target audio tracks can be, for example, digital audio files retrieved by the processing device from local storage on the processing device or from remote storage on a connected device. In an example, the target audio tracks can be streamed to the processing device from a connected device such as a cloud server for an online music service (e.g., Spotify, Apple Music, etc.). In another example, the target audio tracks may be received by the processing device from an audio input such as a microphone. The sources of the target audio tracks can include, for example, an audio signal, digital music file, musical instrument, or environmental sounds.

In example embodiments, the target audio tracks can be in digital form (e.g., MP3, AAC, WAV, etc.), received as an analog signal, generated by a synthesizer or other signal generator, or recorded by one or more microphones or instrument transducers, etc. The target audio tracks may be embodied as a digital music file (.mp3, .wav, .flac, among others) representing sound pressure values, but can also be a data file read by other software which contains parameters or instructions for sound synthesis, rather than a representation of sound itself. The target audio tracks may be individual instruments in a musical composition, groups of instruments (e.g., bussed outputs), but could also be engineered objects such as frequency subbands (e.g., bass frequencies vs treble frequencies). The content of the target audio tracks may include music, but also non-music such as environmental sounds (wind, water, cafe noise, and so on), or any sound signal such as a microphone input.

In example embodiments, to achieve better brain stimulation, target audio tracks may be selected such that they have a wide (i.e., broadband) spectral audio profile—in other words, the target audio tracks can be selected such that they include many frequency components. For example, the target audio tracks may be selected from music composed from many instruments with timbre that produces overtones across the entire range of human hearing (e.g., 20-20 kHz).

Each target audio track in the set of target audio tracks can include one or more modulation characteristics. Non-limiting examples of these modulation characteristics are modulation depth (i.e., energy/strength of modulation at a particular rate or rates), modulation rate (e.g., dominant modulation rate or rates; i.e., local or global maxima in the modulation spectrum), modulation spectrum (i.e., energy at each modulation rate over a range of rates), joint acoustic and modulation frequency (e.g., modulation rates/spectrum in audio frequency sub bands; e.g., modulation spectrum in the bass region vs. treble region), modulation phase relationships across audio frequency bands, spectro-temporal modulation, metadata such as creator tags and/or labelling indicating any of the above even if not measured directly (e.g., metadata can be added to the audio track at the time of creation from parameters used to make the music, etc.), statistical descriptions of the above; first moment and higher-order moments (e.g., mean, variance, skewness, kurtosis, etc. of X), time-varying trajectories of the above (i.e., X over time), derivatives of the above; first order and higher order (instantaneous change, acceleration, etc. of X); etc.

At block 140, the desired modulation characteristic values can be compared with the modulation characteristic values of at least one target audio track from the set of target audio tracks. Various techniques can be used for the comparison. In example embodiments, the processing device can take as input either one or more target audio tracks from the set of target audio tracks to compare against the desired modulation characteristic values. If there are many rated reference audio tracks, each reference audio track's rating value and location in feature space can be considered to define regions in the feature space that are expected to have high ratings (i.e., a user model). This can be framed as a classification problem and can be tackled with any number of methods such as, for example, cluster analysis, decision trees, and/or neural networks.

For example, the difference of 2D modulation spectra (e.g., audio frequency and modulation frequency) between the desired spectrum (as determined by the user model or reference track(s)) and a given target track can be determined by subtraction or by division (% value). Similarly, the difference of 1D modulation spectra (e.g., energy at each modulation frequency across all audio frequencies) can also be determined by subtraction or by division (% value). For example, a 1D modulation spectrum desired by the user model may have normalized power values of 1, 1, 5, 6, 1 at modulation rates of 2 Hz, 4 Hz, 8 Hz, 16 Hz, and 32 Hz, respectively. The 1D modulation spectrum of a first audio track may have normalized power values of 1, 1, 6, 6, 1, at modulation rates of 2 Hz, 4 Hz, 8 Hz, 16 Hz, and 32 Hz, respectively. The 1D modulation spectrum of a second audio track may have normalized power values 2, 3, 6, 10, 1 at modulation rates of 2 Hz, 4 Hz, 8 Hz, 16 Hz, and 32 Hz, respectively. In this example the first audio track, rather than the second audio track, is more similar to the desired spectrum, since the difference of normalized power values is smaller (e.g., 0, 0, 1, 0, 0 versus 1, 2, 1, 4, 0). Similarity in time-averaged properties, versus similarity over time (i.e., average vs. trajectories) can also be used for the comparison.

At block 150, a target audio track can be selected from the set of at least one target audio tracks based on the comparing, wherein the modulation characteristic values of the target audio track best match the desired modulation characteristic values. If the comparing is defined as a function over the space, this may be done by selecting the target audio track with the highest predicted efficacy under a user model (if used). If the model is defined by a single 'best' point or region in the space rather than a function, then determining the best match can be done by finding the closest track (euclidean distance in multiple dimensions). For example, if the model dimensions are modulation depth at 4 Hz and modulation depth at 12 Hz, and if the desired (highest predicted efficacy) under the user model is at a depth of 3 and 7 for 4 Hz and 12 Hz respectively, then an audio track with depths of 4 and 8 at 4 Hz and 12 Hz respectively, would have a calculated euclidean distance from the target of sqrt(($7-3$)^2 ($8-4$)^2)=5.67. This value would be compared against the distance value from other tracks to select the closest target track to the desired modulation characteristic value(s).

Figure 3:
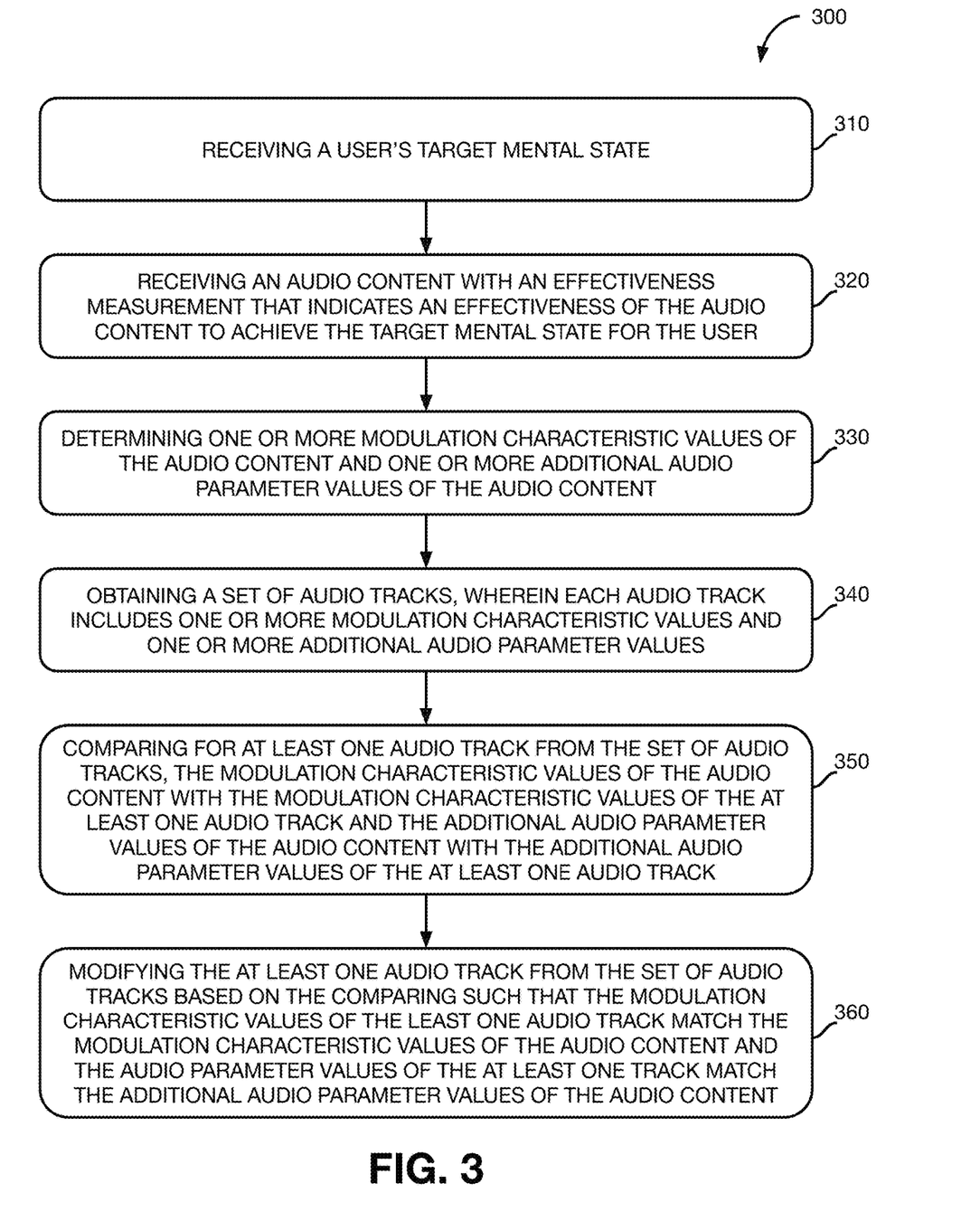
FIG. 3 is a process flowchart according to an example embodiment of the present disclosure.

In some embodiments, the target audio track may be modified as subsequently described in block 360. For example, if the user provides input that they have ADHD, then the user model may indicate that the target audio track should have a spectral slope (treble-bass balance) of 0.6. If, however, the library of target audio tracks contains only audio tracks with spectral slope between 0.1-0.4, then the target audio track with the highest slope (closest to 0.6) may be selected, and further modified to have spectral slope of 0.6. The modification may be done, for example, by low pass filtering.

At block 160, the selected target audio track can be played via one or more audio drivers of one or more playback devices, such as, for example, a smart speaker, a mobile device, a computer/laptop, an ipad, and the like. In one example, the processing device is the same device as the playback device, and the target audio track can be played via audio drivers on the processing device itself. In another example, the processing device can transmit the target audio track (e.g., as a digital file over a data network) to a playback device for playback. In another example, the target audio track can be played on the processing device as well as other playback devices. In another example, the target audio track can be stored (e.g., in a playlist) for future playback.

In example embodiments, the selection of a target audio track for playback at block 160 responsive to the user-associated data at block 110 can be based on a measure of the effectiveness of the user reaching a target mental state with one or more previously played reference audio tracks; these could be tracks included in the library of target tracks but are defined as reference tracks once used as input to the system along with user-associated data (e.g., ratings of those tracks). For example, a target audio track can be selected based on effectiveness rating of previously played reference audio track(s) by the user and modulation characteristics of one or more target audio tracks. This is different from known technology that selects audio tracks based on aesthetic rating and/or music parameters. Another non-limiting example can be that a second audio track is selected for playback based on a first track by implicitly determining (e.g., based on user history, or user devices such as Oura ring that recognizes sleep patterns, etc.,) if the first track is effective. In such a scenario, knowledge of a desired mental state may not be required.

Figure 2:
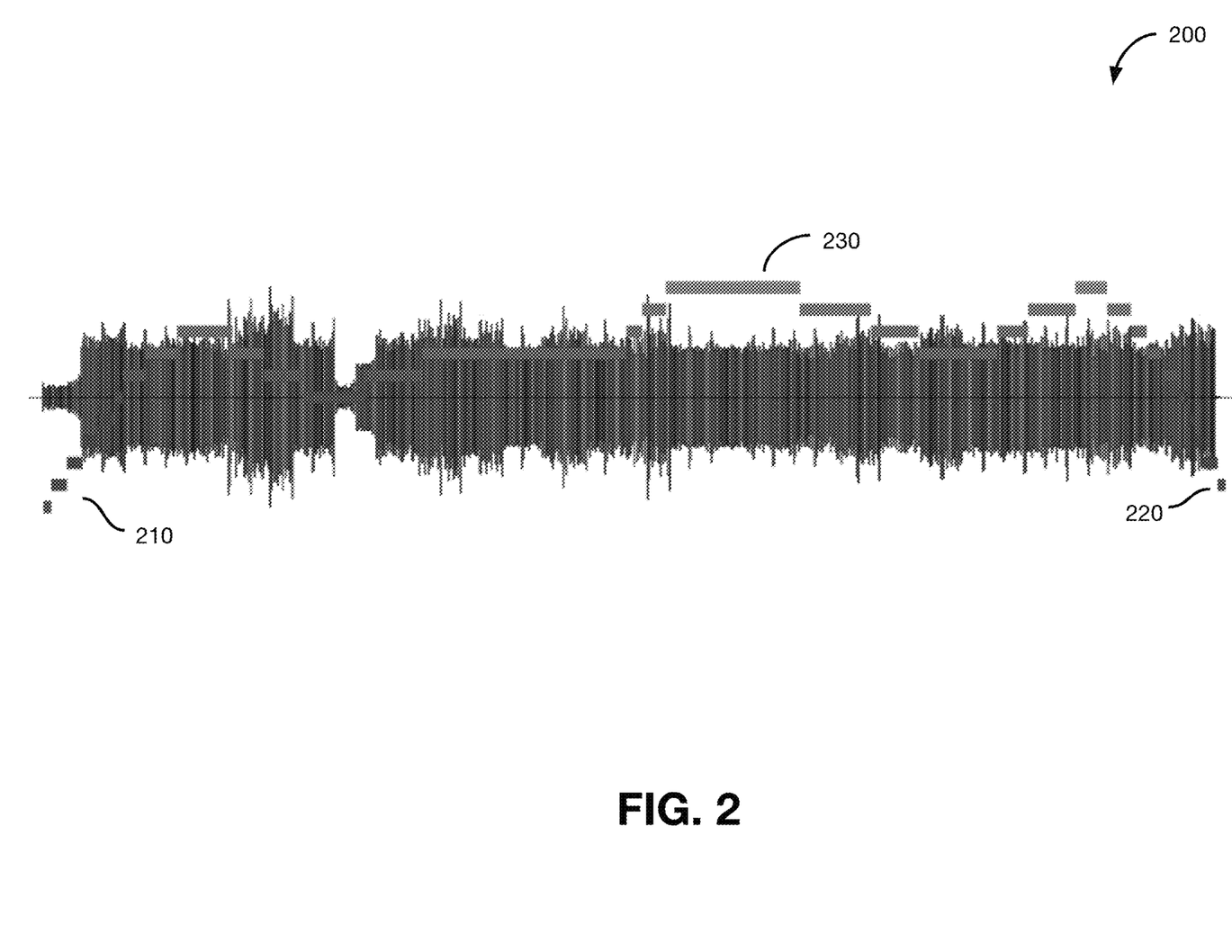
FIG. 2 shows a waveform of an audio track overlaid with its analyzed modulation depth trajectory according to an example embodiment of the present disclosure.

FIG. 2 shows a waveform of an example audio track 205 overlaid with its analyzed modulation depth trajectory according to an embodiment of the present disclosure. In this example, the modulation depth 200 starts low 210, ends low 220, and varies over time during the body of the audio content, with a high plateau 230 starting about halfway through the track. This pattern may be beneficial to provide a targeted mental state such as focus, mediation, relaxation, etc.

FIG. 3 illustrates an example method 300 performed by a processing device (e.g., smartphone, computer, smart speaker, etc.) according to an example embodiment of the present disclosure. According to example embodiments of the present disclosure, method 300 can be performed by the same processing device that performs method 100. Alternatively, method 300 can be performed by a different processing device (e.g., smartphone, computer, etc.). The method 300 may include one or more operations, functions, or actions as illustrated in one or more of blocks 310-360. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

At block 310, a user's target mental state can be received. Certain aspects of block 310 have been previously described with respect to method 100. Non-limiting examples of a user's target mental state can include focus, relax, sleep, and meditate. Each of these example desired mental states can be further distinguished by a target activity and duration. For example, focus can be distinguished by deep work, creative flow, study and read, light work, etc.; relax can be distinguished by chill, recharge, destress, unwind, etc.; sleep can be distinguished by deep sleep, guided sleep, sleep and wake, wind down, etc.; and meditate can be distinguished by unguided and guided. The duration of the mental state may be specified, for example, by a time duration (e.g., minutes, hours, etc.), or a duration triggered by an event (e.g., waking, etc.). The indication may be received via a user interface on a processing device such as, for example, through an interface on the Brain.fm™ application executing on an iPhone™ or Android™ device. Alternatively, and/or additionally, the indication may be received over a network from a different processing device.

At block 320, a reference audio content with an effectiveness measurement can be received. Certain aspects of block 310 have been previously described with respect to method 100. The effectiveness measurement may indicate an effectiveness of the reference audio content to achieve the target mental state for the user. The effectiveness measurement can be implicitly defined as effective by the user merely providing a reference audio content to the system.

At block 330, one or more modulation characteristic values of the reference audio content and one or more additional audio parameter values of the reference audio content can be determined. Certain aspects of block 330 have been previously described with respect to method 100. Non-limiting examples of audio parameters may include tempo; RMS (root mean square energy in signal); loudness; event density; spectrum/spectral/envelope/brightness; temporal envelope; cepstrum (e.g., spectrum of spectrum); chromagram (e.g., what pitches dominate); flux (e.g., change over time); autocorrelation; amplitude modulation spectrum (e.g., how energy distributed over temporal modulation rates); spectral modulation spectrum (e.g., how energy distributed over spectral modulation rates); attack and decay (e.g., rise/fall time of audio events); roughness (e.g., more spectral peaks close together is rougher); harmonicity/inharmonicity (i.e., related to roughness but calculated differently); and/or zero crossings (i.e., sparseness).

Various techniques can be used to identify additional audio parameter values associated with audio content. Non-limiting examples of such techniques can include multi-timescale analysis of features (e.g., different window lengths); analysis of features over time; broadband or within frequency subbands (i.e. after filtering); and/or second order relationships (e.g., flux of cepstrum, autocorrelation of flux). Additionally, or alternatively, additional audio parameter values may be identified in a metadata field associated with audio content.

At block 340, a set of one or more target audio tracks can be obtained such that each target audio track includes one or more modulation characteristic values and one or more additional audio parameter values. Certain aspects of block 340 have been previously described with respect to method 100. In some embodiments, the obtained set of one or more target audio tracks can be based on, for example, a target mental state of the user, an aesthetic perception of whether a reference audio track sounds good, and/or unique properties of a reference audio track relative to others (i.e., distinctiveness).

At block 350, for at least one target audio track from the set of one or more target audio tracks, the one or more modulation characteristic values of the reference audio content can be compared with the one or more modulation characteristic values of the at least one target audio track and the additional one or more audio parameter values of the reference audio content can be compared with the one or more additional audio parameter values of the at least one target audio track. Certain aspects of block 350 have been previously described with respect to method 100.

At block 360, the at least one target audio track from the set of target audio tracks can be modified based on the comparing such that the one or more modulation characteristic values of the at least one target audio track substantially matches the one or more modulation characteristic values of the reference audio content and the one or more audio parameter values of the at least one target audio track substantially matches the one or more additional audio parameter values of the reference audio content. For example, if a user with ADHD prefers listening to a particular pop song to focus, then the modulation characteristics of that pop song can be modified (e.g. change the modulation depth to 12-20 Hz) based on the target "focus" mental state for the user. In one embodiment where the selected target audio track is sufficiently similar in the comparing, block 360 can be omitted.

In an example embodiment, the processing device may select a subsequent target audio track from the set of target audio tracks based on the comparing (as described by block 350) such that the modulation characteristic values of a beginning portion of the subsequent target audio track aligns in a predetermined manner with an end portion of the reference audio track. In this case the processing device may use the heads and tails of audio tracks instead of the entire track. The processing device may then sequentially combine, or chain, the reference audio track and the subsequent selected target audio track. When the audio tracks are combined, the start and end regions (e.g., where modulation depth is low) can be removed to avoid a dip in modulation depth (e.g., potentially disrupting the effect of modulation). The resulting combination of audio tracks can have more consistent modulation depth and may be valuable to the user by maintaining the desired mental state.

In one embodiment, heads and tails of audio tracks can be used to chain audio tracks together to create a playlist with modulation characteristics and/or other audio characteristics (e.g., as described above) that are smooth and continuous across track changes. In another embodiment, audio tracks can be chained based on contrasting (i.e., maximally different) modulation characteristics and/or other audio characteristics. In yet another embodiment, target audio tracks can be chained based on a combination of both contrasting and similar modulation characteristics and/or other audio characteristics.

In an example embodiment, an acoustic analysis can be performed on the modified target audio content. The analysis can include determining a distance, in measurement space (i.e., the space of measured modulation characteristics and/or audio characteristics), between the modified target audio content and a reference audio content. The determined distance can define a cost function in the space of modifiable parameters. The cost function can then be evaluated by applying optimization techniques, which can involve selecting multiple sample points in the parameter space, modifying the audio, and finding the distance in measurement space at each sampled point in the parameter space. The target audio content can also be modified repeatedly until a global minimum in the cost function can be adequately estimated. The target audio content can then be further modified according to the estimated optimum parameters or the modified target audio can be retrieved if already close to this optimum.

Alternatively, in an example embodiment, a mapping can be provided that translates between parameter space and measurement space such that a movement in parameter space would result in a known movement in measurement space. Similarly, the parameter space and measurement space can be chosen to be heavily interrelated, e.g., if the parameter space is the depth and rate of broadband tremolo, and the measurement space is the depth and rate of broadband modulation. In these cases, the optimization over a latent function (i.e., minimization of the cost function defined by the reference-target difference in measurement space at each point in the target-modification parameter space) is not required since the location of the modified target in measurement space can be estimated directly by the change in parameters during modification.

In example embodiments, one or more target audio tracks can be modified to move toward a particular location in a significant feature space, e.g., modulation depth and rate.

The parameter space, e.g., the many knobs that can be turned to modify the audio, may not be the same as the measurement space (feature space), which relates the music to effects on the brain.

In example embodiments, the set of one or more target audio tracks can include a single target audio track only. In such a case, that single target audio track can be modified along various dimensions as described with respect to block 360. The modulation characteristic of the single target audio track can be modified based on user inputs (e.g., prescribed modulation characteristics values). For example, if a user completes a survey that shows they have ADHD, and it is known that they will benefit from a particular modulation depth at 12-20 Hz rate, then the user can select the closest target audio track from a library of target audio tracks. The selected target audio track may still not be ideal. In such a case, the target audio track can be modified to have the desired modulation characteristics values.

Figure 4A:
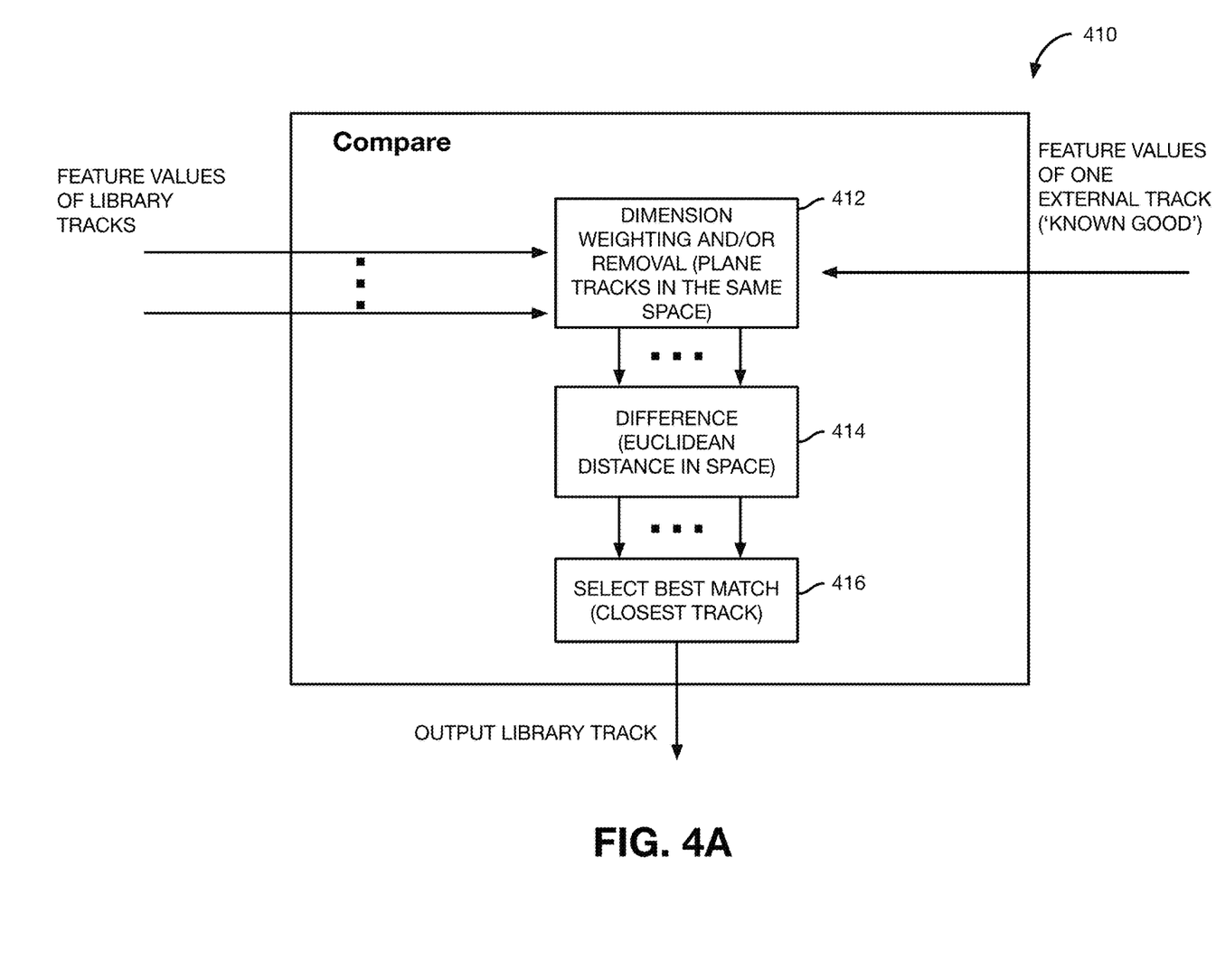
FIG. 4A is a process flowchart according to an example embodiment of the present disclosure.

FIG. 4A provides an example illustration of the comparison process flow 410 as previously described with respect to block 350 of method 300, when using a single reference track rather than a user model. The process flows 410 may include one or more operations, functions, or actions as illustrated in one or more of blocks 412-416. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

As shown in FIG. 4A, feature values of the target audio tracks 411 and feature values of the reference audio tracks 413 are input to the comparison block 410. In this example, a dimension weighting and/or removal block 412 takes these input values and determines which feature dimensions (if any) should be reweighted or removed to establish a feature space that is common to the target and reference tracks, and is most relevant to the user's desired mental state. For example, if only the reference track(s) have an analyzed dimension of 'modulation phase', but the target track does not, this dimension could be removed prior to comparison. Similarly, if the user is known to want a mental state of Focus, but analyzed dimensions exist that are known to be irrelevant to focus, these dimensions could be removed by process 412/422 prior to comparison in blocks 414/424.

A difference block 414 takes the output of dimension weighting and/or removal block 412 and determines the difference (e.g., in Euclidean distance space) between reference and targets. In an example embodiment, modification 360 may not move a target audio track arbitrarily in feature space; there are limited directions and distances based on audio processing techniques, the target audio track to be modified, and other constraints. For example, consider one rated audio track T and two audio tracks A and B in a library of audio tracks. In this example, it may be the case that T-A>T-B (i.e., the difference between T and A is greater than the difference between T and B; so, B seems best), but the distance T-B cannot be traversed by available audio modification techniques, whereas T-A can be traversed by available audio modification techniques. A practical example may be if T and A differ greatly in brightness (e.g., spectral tilt), which can be modified by filtering/EQ without impacting other dimensions, whereas T and B differ in the phase of modulation across frequency bands, which is not easy to modify (e.g., may require removing instruments, etc). In this case, B may be selected as being more similar in the process 410 (method 100), but A may be selected for modification in the process 420 (method 300). In block 416, the best match is selected and the target audio track is output 415.

Figure 4B:
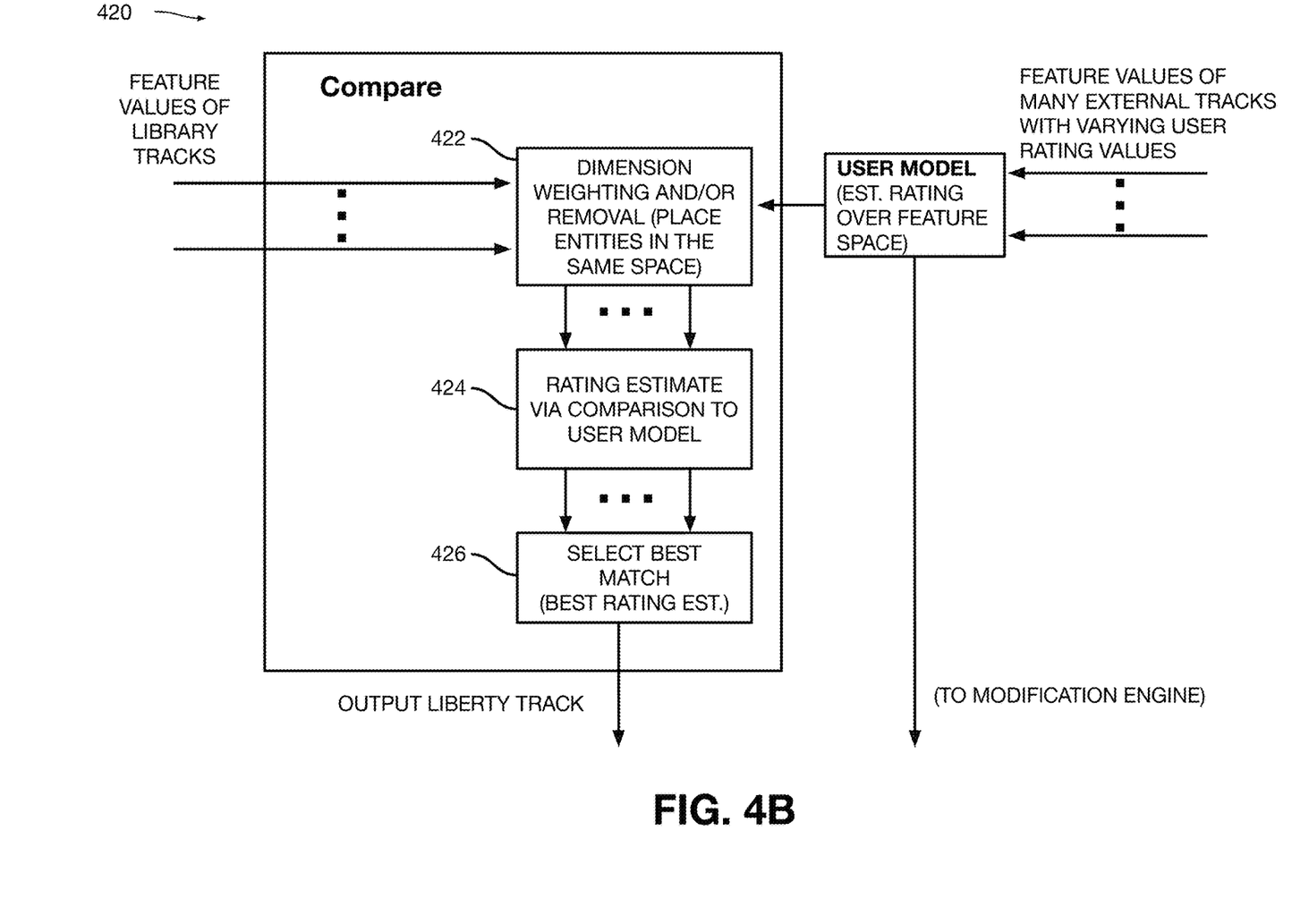
FIG. 4B is a process flowchart according to an example embodiment of the present disclosure.

FIG. 4B provides an example illustration of the comparison process flow 420 as previously described with respect to block 350 of method 300, when a user model is used The process flows 410, 420 may include one or more operations, functions, or actions as illustrated in one or more of blocks 412-426. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

Unlike in method 100, method 300 may consider how modification can move a target audio track through the feature space. Thus, process 422, in addition to establishing a common feature space between target and reference as in process 412, may reweight the feature space to reflect the possibilities of movement by audio modification. For example, a dimension corresponding to brightness (e.g., which may be easy to manipulate) may be compressed such that a difference in that dimension is down-weighted in the comparison. This allows process 420 to find a target audio track which can be modified to be the best match 426 (optimal features under the user model), whereas process 410 aims to find a target audio track that substantially matches the desired modulation characteristics 416 (closest match to a reference track known to have desirable characteristics).

Figure 5:
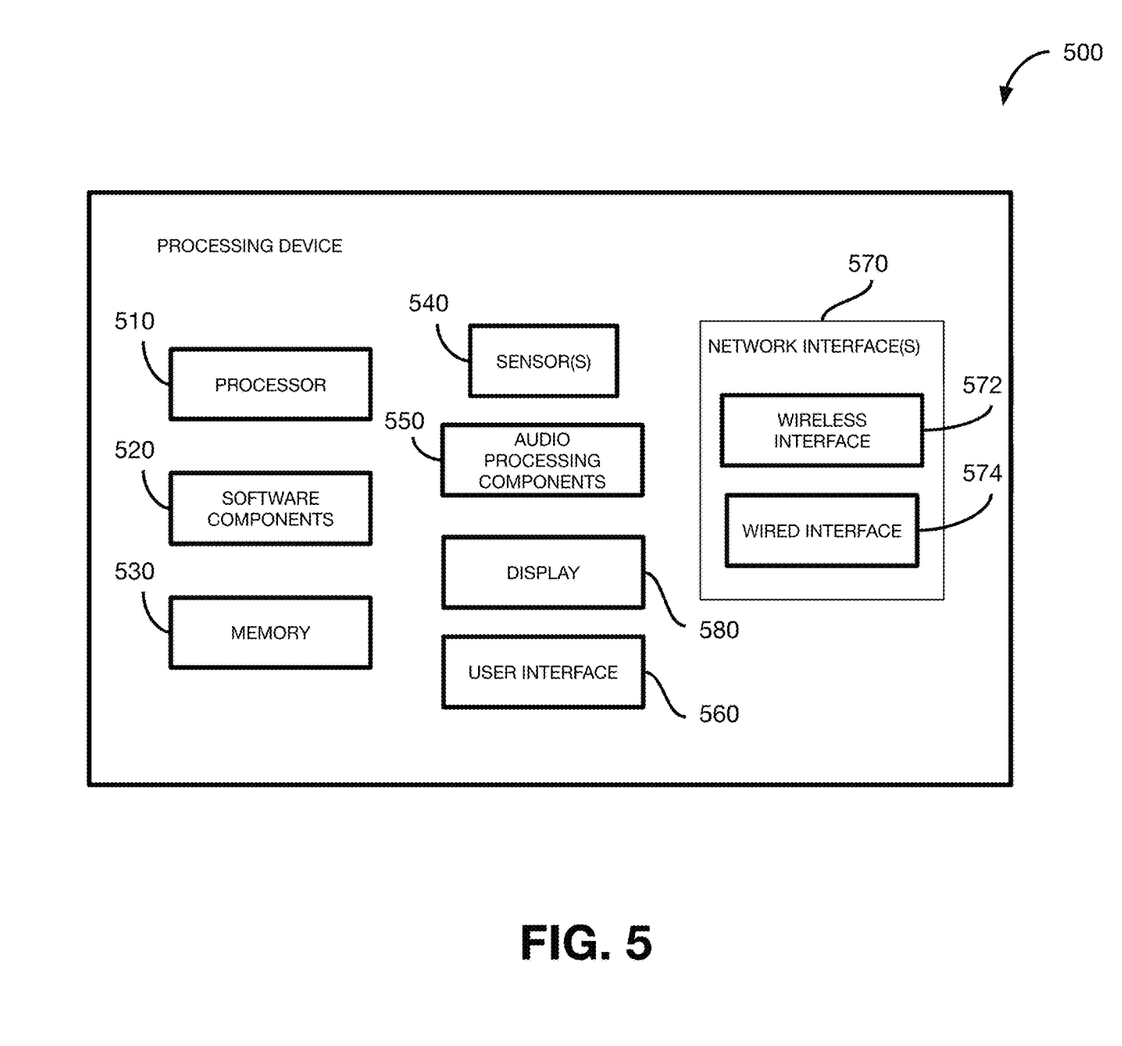
FIG. 5 is a functional block diagram of a processing device according to an example embodiment of the present disclosure.

FIG. 5 shows a functional block diagram of an example processing device 500 that can implement the previously described methods 100 and 300 and process flows 410 and 520. The processing device 500 includes one or more processors 510, software components 520, memory 530, one or more sensor inputs 540, audio processing components (e.g. audio input) 550, a user interface 560, a network interface 570 including wireless interface(s) 572 and/or wired interface(s) 574, and a display 580. The processing device may further optionally include audio amplifier(s) and speaker(s) for audio playback. In one case, the processing device 500 may not include the speaker(s), but rather a speaker interface for connecting the processing device to external speakers. In another case, the processing device 500 may include neither the speaker(s) nor the audio amplifier (s), but rather an audio interface for connecting the processing device 500 to an external audio amplifier or audio-visual playback device.

In some examples, the one or more processors 510 include one or more clock-driven computing components configured to process input data according to instructions stored in the memory 530. The memory 530 may be a tangible, non-transitory computer-readable medium configured to store instructions executable by the one or more processors 510. For instance, the memory 530 may be data storage that can be loaded with one or more of the software components 520 executable by the one or more processors 510 to achieve certain functions. In one example, the functions may involve the processing device 500 retrieving audio data from an audio source or another processing device. In another example, the functions may involve the processing device 500 sending audio data to another device or a playback device on a network.

The audio processing components 550 may include one or more digital-to-analog converters (DAC), an audio preprocessing component, an audio enhancement component or a digital signal processor (DSP), and so on. In one embodiment, one or more of the audio processing components 550 may be a subcomponent of the one or more processors 510. In one example, audio content may be processed and/or intentionally altered by the audio processing components 550 to produce audio signals. The produced audio signals may be further processed and/or provided to an amplifier for playback.

The network interface 570 may be configured to facilitate a data flow between the processing device 500 and one or more other devices on a data network, including but not limited to data to/from other processing devices, playback devices, storage devices, and the like. As such, the processing device 500 may be configured to transmit and receive audio content over the data network from one or more other devices in communication with the processing device 500, network devices within a local area network (LAN), or audio content sources over a wide area network (WAN) such as the Internet. The processing device 500 may also be configured to transmit and receive sensor input over the data network from one or more other devices in communication with the processing device 500, network devices within a LAN or over a WAN such as the Internet. The processing device 500 may also be configured to transmit and receive audio processing information such as, for example, a sensor-modulation-characteristic table over the data network from one or more other devices in communication with the processing device 500, network devices within a LAN or over a WAN such as the Internet.

As shown in FIG. 5, the network interface 570 may include wireless interface(s) 572 and wired interface(s) 574. The wireless interface(s) 572 may provide network interface functions for the processing device 500 to wirelessly communicate with other devices in accordance with a communication protocol (e.g., any wireless standard including IEEE 802.11a/b/g/n/ac, 802.15, 4% mobile communication standard, and so on). The wired interface(s) 574 may provide network interface functions for the processing device 500 to communicate over a wired connection with other devices in accordance with a communication protocol (e.g., IEEE802.3). While the network interface 570 shown in FIG. 5 includes both wireless interface(s) 572 and wired interface (s) 574, the network interface 570 may in some embodiments include only wireless interface(s) or only wired interface(s).

The processing device may include one or more sensor(s) 540. The sensors 540 may include, for example, inertial sensors (e.g., accelerometer, gyrometer, and magnetometer), a microphone, a camera, or a physiological sensor such as, for example, a sensor that measures heart rate, blood pressure, body temperature, EEG, MEG, Near infrared (fNIRS), or bodily fluid. In some example embodiments, the sensor may correspond to a measure of user activity on a device such as, for example, a smart phone, computer, tablet, or the like.

The user interface 560 and display 580 can be configured to facilitate user access and control of the processing device. Example user interface 560 include a keyboard, touchscreen on a display, navigation device (e.g., mouse), etc.

Figure 6:
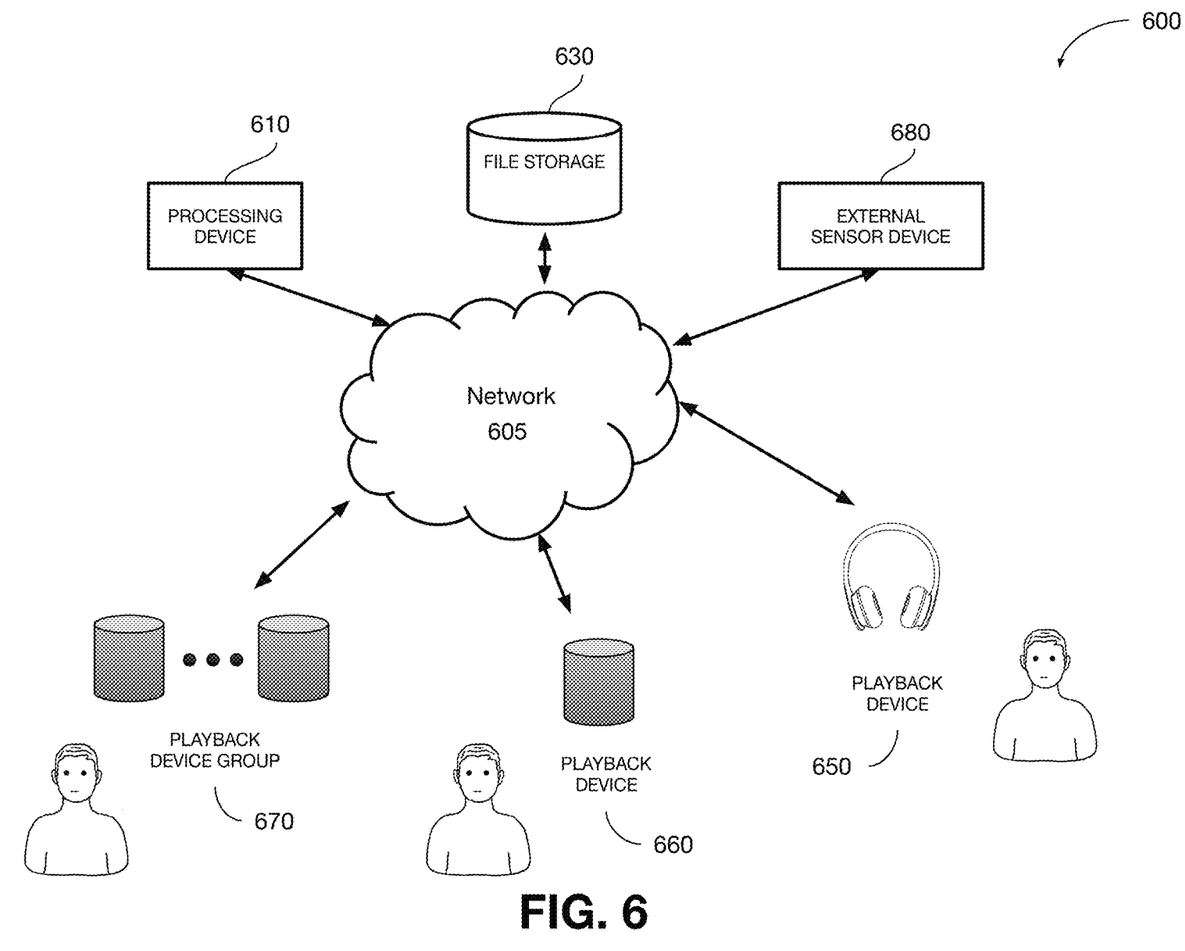
FIG. 6 is an example system with various components according to an example embodiment of the present disclosure.

Aspects of the present disclosure may exist in part or wholly in, distributed across, or duplicated across one or more physical devices. FIG. 6 illustrates one such example system 600 in which the present invention may be practiced. The system 600 illustrates several devices (e.g., processing device 610, audio processing device 620, file storage 630, playback device 650, 660, and playback device group 670) interconnected via a data network 605. Although the devices are shown individually, the devices may be combined into fewer devices, separated into additional devices, and/or removed based upon an implementation. The data network 605 may be a wired network, a wireless network, or a combination of both.

In some example embodiments, the system 600 can include an audio processing device that can perform various functions, including but not limited to audio processing. In an example embodiment, the system 600 can include a processing device 610 that can perform various functions, including but not limited to, aiding the processing by the audio processing device 620. In an example embodiment, the processing devices 610 can be implemented on a machine such as the previously described system 500.

In an example embodiment, the system 600 can include a storage 630 that is connected to various components of the system 600 via a network 605. The connection can also be wired (not shown). The storage 630 can be configured to store data/information generated or utilized by the presently described techniques. For example, the storage 630 can store the set of one or more target audio tracks, as previously discussed with respect to the steps 130 and 340. The storage 630 can also store the audio track in the step 160.

In an example embodiment, the system 600 can include one or more playback devices 650, 660 or a group of playback devices 670 (e.g. playback devices, speakers, mobile devices, etc.). These devices can be used to playback the audio output, as previously described in the step 180. In some example embodiments, a playback device may include some or all of the functionality of the processing device 610, the audio processing device 620, and/or the file storage 630. As described previously, a sensor can be based on the audio processing device 620 or it can be an external sensor device 680 and data from the sensor can be transferred to the audio processing device 620.

Additional examples of the presently described method and device embodiments are suggested according to the structures and techniques described herein. Other non-limiting examples may be configured to operate separately or can be combined in any permutation or combination with any one or more of the other examples provided above or throughout the present disclosure.

It will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

It should be noted that the terms "including" and "comprising" should be interpreted as meaning "including, but not limited to". If not already set forth explicitly in the claims, the term "a" should be interpreted as "at least one" and "the", "said", etc. should be interpreted as "the at least one", "said at least one", etc. Furthermore, it is the Applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

The invention claimed is:

1. A method comprising:
receiving, by a processing device, user-associated data related to a user;
determining, by the processing device, one or more desired modulation characteristic values for an audio track based on the user-associated data, wherein the desired modulation characteristic values for the audio track comprise a desired modulation depth at a desired modulation rate;
obtaining, by the processing device, a set of one or more target audio tracks, wherein each target audio track has a modulation depth at a modulation rate;
comparing, by the processing device, the desired modulation characteristic values with the modulation characteristic values of the target audio tracks in the set of one or more target audio tracks;
selecting, by the processing device, a target audio track from the set of one or more target audio tracks based on the comparing, wherein at least the modulation depth of the selected target audio track at the desired modulation rate for the audio track substantially match the desired modulation depth for the audio track at the desired modulation rate for the audio track; and
playing, by the processing device, the selected target audio track.

2. The method of claim 1, wherein the user-associated data comprises a self-report user data and/or a target mental state of the user.

3. The method of claim 2, wherein the self-report user data comprises user information regarding sound sensitivity, age, ability to focus, work style, ADHD, and/or preferences for a reference audio track.

4. The method of claim 2, wherein the target mental state comprises focus, relax, sleep, exercise, and/or meditation.

5. The method of claim 1, wherein the user-associated data comprises a reference audio content with an effectiveness measurement, wherein the effectiveness measurement indicates an effectiveness of the reference audio content for the user.

6. The method of claim 5, comprising:
determining one or more modulation characteristic values of the reference audio content, by the processing device, based on modulation synthesis parameters and/or modulation domain analysis.

7. The method of claim 1, comprising:
modifying, by the processing device, the one or more modulation characteristic values of the selected target audio track to match the desired modulation characteristic values.

8. The method of claim 1, wherein the desired modulation depth at a desired modulation rate comprises a desired modulation depth of between about 0.2 to 8 at a modulation rate between about 2 Hz and 32 Hz.

9. A method comprising:
receiving, by a processing device, a target mental state for a user;
receiving, by the processing device, a reference audio content with an effectiveness measurement that indicates an effectiveness of the reference audio content to achieve the target mental state for the user;
determining, by the processing device, one or more modulation characteristic values of the reference audio content and one or more additional audio parameter values of the reference audio content, wherein the one or more modulation characteristic values of the reference audio content include a modulation depth at a modulation rate;
obtaining, by the processing device, a set of one or more target audio tracks, wherein each target audio track includes one or more modulation characteristic values and one or more additional audio parameter values;
comparing, by the processing device, for at least one target audio track from the set of one or more target audio tracks, the modulation characteristic values of the reference audio content with the modulation characteristic values of the at least one target audio track and the additional audio parameter values of the reference audio content with the additional audio parameter values of the at least one target audio track; and modifying, by the processing device, the at least one target audio track from the set of one or more target audio tracks based on the comparing such that, after modifying the at least one target audio track, the modulation characteristic values of the modified at least one target audio track comprise a modulation depth at a modulation rate that substantially matches a modulation depth at a modulation rate of the reference audio content and at least one of the audio parameter values of the at least one target audio track substantially match the additional audio parameter values of the reference audio content.

10. The method of claim 9, wherein the modifying comprises dynamically adding modulation characteristics to the target audio content.

11. The method of claim 9, comprising:
selecting, by the processing device, a subsequent target audio track from the set of one or more target audio tracks based on the comparing, wherein modulation characteristic values of a beginning portion of the subsequent target audio track aligns in a predetermined manner with modulation characteristic values of an end portion of the at least one target audio track; and
chaining, by the processing device, the at least one target audio track and the subsequent target audio track.

12. A device comprising a processor and associated memory, the processor being configured to:
receive user-associated data related to a user;
determine one or more desired modulation characteristic values for an audio track based on the user-associated data, wherein the desired modulation characteristic values for the audio track comprise a desired modulation depth at a desired modulation rate;
obtain a set of one or more target audio tracks, wherein each target audio track has a modulation depth at a modulation rate;
compare the desired modulation characteristic values with the modulation characteristic values of the audio tracks in the set of one or more target audio tracks;
select a target audio track from the set of one or more target audio tracks based on the comparing, wherein at least the modulation depth of the selected audio track at the desired modulation rate of the audio track substantially match the desired modulation depth for the audio track at the desired modulation rate for the audio track; and
play the selected audio track.

13. The device of claim 12, wherein the user-associated data comprises a self-report user data and/or a target mental state of the user.

14. The device of claim 13, wherein the self-report user data comprises user information regarding sound sensitivity, age, ability to focus, work style, ADHD, and/or preferences for a reference audio track.

15. The device of claim 13, wherein the target mental state comprises focus, relax, sleep, exercise, and/or meditation.

16. The device of claim 12, wherein the user-associated data comprises a reference audio content with an effectiveness measurement, wherein the effectiveness measurement indicates an effectiveness of the reference audio content for the user.

17. The device of claim 16, wherein the processor is configured to determine one or more modulation characteristic values of the reference audio content based on modulation synthesis parameters and/or modulation domain analysis.

18. The device of claim 17, wherein the processor is configured to modify the one or more modulation characteristic values of the selected target audio track to match the desired modulation characteristic values based on the effectiveness measurement of the reference audio content.

19. A device comprising a processor and associated memory, wherein the device is configured to:
receive data corresponding to a user's target mental state;
receive a reference audio content with an effectiveness measurement that indicates an effectiveness of the reference audio content to achieve the target mental state for the user;
determine one or more modulation characteristic values of the reference audio content and/or one or more additional audio parameter values of the reference audio content, wherein the one or more modulation characteristic values of the reference audio content include a modulation depth at a modulation rate;
obtain a set of one or more target audio tracks, wherein each target audio track includes one or more modulation characteristic values and one or more additional audio parameter values;
compare, for at least one target audio track from the set of one or more target audio tracks, the modulation characteristic values of the reference audio content with the modulation characteristic values of the at least one target audio track and the additional audio parameter values of the reference audio content with the additional audio parameter values of the at least one target audio track; and
modify the at least one target audio track from the set of one or more target audio tracks based on the comparing such that, after modifying the at least one target audio track, the modulation characteristic values of the modified at least one target audio track comprise a modulation depth at a modulation rate that substantially matches a modulation depth at a modulation rate of the reference audio content and at least one of the audio parameter values of the at least one target audio track substantially match the additional audio parameter values of the reference audio content.

20. The device of claim 19, wherein to modify the at least one target audio track, the processor is configured to dynamically add modulation characteristics to the at least one target audio track.

21. The device of claim 19, wherein the processor is configured to:
select a subsequent target audio track from the set of one or more target audio tracks based on the comparing, wherein modulation characteristic values of a beginning portion of the subsequent target audio track aligns in a predetermined manner with modulation characteristic values of an end portion of the at least one target audio track; and
chain the at least one target audio track and the subsequent target audio track.

* * * * *